(12) United States Patent
Molnar et al.

(10) Patent No.: US 12,343,426 B2
(45) Date of Patent: *Jul. 1, 2025

(54) THERAPEUTIC HYDROGELS

(71) Applicant: Boston Scientific Scimed Inc., Maple Grove, MN (US)

(72) Inventors: Viktoria Molnar, Macroom (IE); Carolina Villarreal, Hopedale, MA (US); Bhanu Prasanth Koppolu, Cary, NC (US); Nivedita Swetha Ramkumar, Cork (IE); Philip David Dorgan, Cork (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 332 days.

This patent is subject to a terminal disclaimer.

(21) Appl. No.: 17/713,596

(22) Filed: Apr. 5, 2022

(65) Prior Publication Data

US 2022/0313603 A1 Oct. 6, 2022

Related U.S. Application Data

(60) Provisional application No. 63/171,231, filed on Apr. 6, 2021.

(51) Int. Cl.
| | | |
|---|---|---|
| *A61K 9/06* | (2006.01) | |
| *A61K 47/02* | (2006.01) | |
| *A61K 47/36* | (2006.01) | |
| *A61K 47/42* | (2017.01) | |

(52) U.S. Cl.
CPC ............... *A61K 9/06* (2013.01); *A61K 47/02* (2013.01); *A61K 47/36* (2013.01); *A61K 47/42* (2013.01)

(58) Field of Classification Search
CPC .......... A61K 9/06; A61K 47/02; A61K 47/36; A61K 47/42; A61K 9/0019; A61L 2400/06; A61L 24/001; A61L 27/26; A61L 27/50; A61L 27/52; A61L 31/041; A61L 31/145; A61L 24/0031; A61L 24/043; A61L 31/14
See application file for complete search history.

(56) References Cited

U.S. PATENT DOCUMENTS

| | | |
|---|---|---|
| 4,789,501 A | 12/1988 | Day et al. |
| 6,172,219 B1 | 1/2001 | Callegaro et al. |
| 6,203,680 B1 | 3/2001 | Cole |
| 7,326,324 B2 | 2/2008 | Thorne et al. |
| 9,012,415 B2 | 4/2015 | Da Silva Correia et al. |
| 2011/0159068 A1 | 6/2011 | Soula et al. |
| 2019/0330384 A1 | 10/2019 | Romero Amandi De Sousa et al. |

FOREIGN PATENT DOCUMENTS

| | | |
|---|---|---|
| CN | 107753421 B | 2/2021 |
| EP | 2366386 A1 | 9/2011 |
| JP | 2012-506900 A | 3/2012 |
| JP | 2020-516311 A | 6/2020 |
| WO | 2005087274 A1 | 9/2005 |
| WO | 2008067518 A2 | 6/2008 |
| WO | 2015069634 A1 | 5/2015 |
| WO | 2016082045 A1 | 6/2016 |
| WO | 2017-089974 A1 | 6/2017 |

OTHER PUBLICATIONS

Zhang et al. ACS Appl Mater. 2018; 10: 6879-6886. (Year: 2018).*
Usach et al. Adv Ther. 2019; 36: 2986-2996. (Year: 2019).*
International Search Report and Written Opinion dated Jul. 14, 2022 for International Application No. PCT/US2022/023457.
Koivisto et al; "Bioamine-Crosslinked Gellan Gum Hydrogel for Neural Tissue Engineering," Biomedical Materials, vol. 12, pp. 1-16. 2017.
Kingsley et al; "Microcapsules and 3D customizable shelled microenvironments from laser direct-written microbeads," Biotechnology and Bioengineering, 2016, 113, 2264-2274, DOI: 10.1002/bit.25987.
Kosik et al; "Electrolyte alginate/poly-l-lysine membranes for connective tissue development," Materials Letters, 2016, 184, 104-107, DOI: 10.1016/j.matlet.2016.08.032.
Lopez-Cebral et al; "Spermidine-Cross-linked Hydrogels as Novel Potential Platforms for Pharmaceutical Applications," Journal of Pharmaceutical Sciences, 2013, 102, 2632-2643, DOI: 10.1002/jps.23631.
Nunamaker et al; "In vivo stability and biocompatibility of implanted calcium alginate disks," Journal of Biomedical Materials Research Part A, 83, 2007, 1128-1137, DOI: 10.1002/jbm.a.31275.

* cited by examiner

*Primary Examiner* — David Browe
(74) *Attorney, Agent, or Firm* — Seager, Tufte & Wickhem, LLP

(57) ABSTRACT

The present disclosure pertains to therapeutic hydrogels that comprise an anionic polysaccharide crosslinked by a branched polyamine, wherein the branched polyamine comprises at least two primary amine groups, more typically at least three primary amine groups. The present disclosure also pertains to medical compositions that comprise such therapeutic hydrogels and to methods of medical treatment in which such therapeutic hydrogels are delivered to a patient in need of medical treatment.

20 Claims, 1 Drawing Sheet

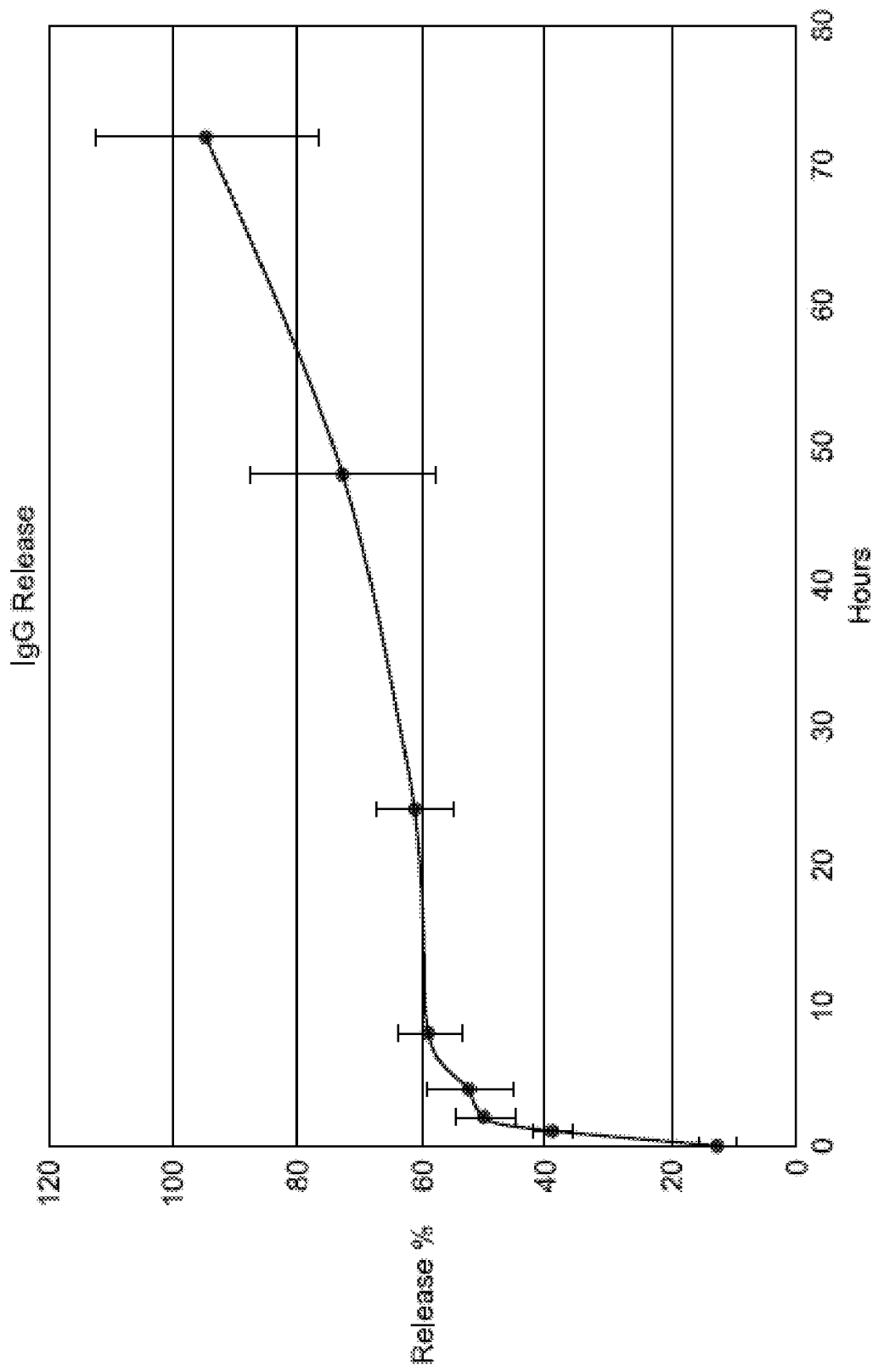

THERAPEUTIC HYDROGELS

CROSS-REFERENCE TO RELATED APPLICATION DESCRIPTION

This application claims the benefit of U.S. Provisional Patent Application Ser. No. 63/171,231 filed on Apr. 6, 2021, the disclosure of which is incorporated herein by reference.

BACKGROUND

Various therapeutic hydrogels are known in the medical arts, which hydrogels may be used in a wide variety of medical applications.

The present disclosure relates to polysaccharide-based therapeutic hydrogels that can be in various medical applications. The therapeutic hydrogels of the present disclosure can be used, for example, in conjunction with embolic agents, tissue sealants, tissue spacers, tissue augmentation compositions, scaffolds for tissue regeneration and/or cellular growth, surgical adhesion prevention barriers, and implantable wound dressings, among other uses.

SUMMARY

The present disclosure relates to therapeutic hydrogels that comprise an ionic polysaccharide and a branched polyamine. The therapeutic hydrogels can be used in various medical applications.

In some embodiments, the disclosure relates to therapeutic hydrogels that comprise an anionic polysaccharide crosslinked by a branched polyamine that comprises at least three primary amine groups.

In some embodiments, the disclosure relates to therapeutic hydrogels that comprise (a) an anionic polysaccharide and (b) a branched polyamine, wherein the anionic polysaccharide is negatively charged at a pH of the therapeutic hydrogel, wherein the branched polyamine is positively charged and comprises two or more positively charged primary amine groups at the pH of the therapeutic hydrogel, and wherein the branched polyamine ionically crosslinks the anionic polysaccharide.

In some embodiments, which can be used in conjunction with any of the preceding embodiments, the therapeutic hydrogel may have a pH that ranges from 5.5 to 7.5.

In some embodiments, which can be used in conjunction with any of the preceding embodiments, the branched polyamine may be in the form of an organic acid salt or in the form of an inorganic salt, the branched polyamine may have a molecular weight that is less than 2000, the branched polyamine may be an oligomeric branched polyamine having from 2 to 10 monomer residues, or the branched polyamine may have any combination of the foregoing characteristics.

In some embodiments, which can be used in conjunction with any of the preceding embodiments, the anionic polysaccharide may be a linear anionic polysaccharide or a branched anionic polysaccharide.

In some embodiments, which can be used in conjunction with any of the preceding embodiments, the therapeutic hydrogel is a flowable therapeutic hydrogel, or the therapeutic hydrogel has a free-standing three-dimensional shape.

In some embodiments, which can be used in conjunction with any of the preceding embodiments, therapeutic hydrogel further comprises an imaging agent, which may be selected, for example, from fluorescent dyes, magnetic resonance imaging (MRI) contrast agents, ultrasound contrast agents, radiocontrast agents, and near-infrared (NIR) contrast agents.

In some embodiments, which can be used in conjunction with any of the preceding embodiments, the therapeutic hydrogel further comprises a cation selected from Group I metal cations and Group II metal cations.

In some embodiments, which can be used in conjunction with any of the preceding embodiments, the therapeutic hydrogel of further comprises chitosan.

In some embodiments, which can be used in conjunction with any of the preceding embodiments, the therapeutic hydrogel further comprises a therapeutic agent. For example, therapeutic agent delivery depots may be provided, which comprise such therapeutic hydrogels.

In some embodiments, the present disclosure provides medical compositions that comprise therapeutic hydrogels in accordance with any of the preceding embodiments. Examples of such medical compositions include, for instance, embolic agents, tissue sealants, tissue spacers, tissue augmentation compositions, scaffolds for tissue regeneration and/or cellular growth, surgical adhesion prevention barriers, and implantable wound dressings, among others.

In some embodiments, the present disclosure provides methods of treatment that comprise delivering therapeutic hydrogels in accordance with any of the preceding embodiments to a patient. Such methods include, for example, methods of local or systemic therapeutic agent release, methods of tissue embolization, methods of spacing a first tissue from a second tissue, methods of sealing tissue, methods of preventing surgical adhesions, methods of tissue augmentation, methods of regenerating tissue, and methods of hemostasis, among others.

BRIEF DESCRIPTION OF THE DRAWING

The FIGURE illustrates cumulative release % of IgG as a function of time from a therapeutic hydrogel, in accordance with an embodiment of the present disclosure.

DETAILED DESCRIPTION

The present disclosure relates to therapeutic hydrogels that comprise an ionic polysaccharide and a branched polyamine. The therapeutic hydrogels can be used in various medical applications.

In various embodiments, the therapeutic hydrogels of the present disclosure include an ionic polysaccharide crosslinked by a branched polyamine, wherein the branched polyamine has at least 3 primary amine groups. In some of these embodiments, the branched polyamine has three, four, five, six, seven, eight, nine, ten, or more primary amine groups per molecule. In some of these embodiments, the branched polyamine may have between three and twenty-five, between three and twenty, between three and fifteen, between three and ten, or between three and five primary amine groups.

In various embodiments, the therapeutic hydrogels of the present disclosure include: (a) an anionic polysaccharide and (b) a branched polyamine, wherein the branched polyamine is positively charged and has two or more positively charged primary amine groups at pH of the therapeutic hydrogels such that the branched polyamine ionically crosslinks the anionic polysaccharide. In some of these embodiments, the branched polyamine has three or more positively charged primary amine groups per molecule at the pH of the therapeutic hydrogels. In some of these embodiments the branched polyamine has three, four, five, six, seven, eight, nine, ten, or more positively charged primary amine groups per molecule at the pH of the therapeutic hydrogels. In some of these embodiments the branched polyamine between three and twenty-five, between three and twenty, between three and fifteen, between three and ten, or between three and five positively charged primary amine groups per molecule at the pH of the therapeutic hydrogels.

In some embodiments, the pH of the therapeutic hydrogels of any of the preceding embodiments may range from 5.5 to 7.5.

In some embodiments, the branched polyamine of the therapeutic hydrogels of any of the preceding embodiments may have a molecular weight that is less than 2000 g/mol. For example, the branched polyamine may range from 100 g/mol to 250 g/mol to 500 g/mol to 750 g/mol to 1000 g/mol to 1250 g/mol to 1500 g/mol to 2000 g/mol in molecular weight (in other words, the molecular weight of the branched polyamine may range between any two of the preceding values).

In some embodiments, the therapeutic hydrogels of any of the preceding embodiments may contain from 0.005 w/w % or less to 5 w/w % or more branched polyamine, for example, ranging from 0.005 w/w % to 0.01 w/w % to 0.025 w/w % to 0.05 w/w % to 0.10 w/w % to 0.25 w/w % to 0.5 w/w % to 1.0 w/w % to 2.5 w/w % to 5 w/w % branched polyamine.

In some embodiments, the branched polyamine of the therapeutic hydrogels of any of the preceding embodiments may be an oligomeric branched polyamine having from 2 to 10 monomer residues. For example, the oligomeric branched polyamine may be a branched peptide oligomer that comprises a plurality of lysine residues or the oligomeric branched polyamine may be a branched polyethyleneimine oligomer, among other possibilities.

In some embodiments, the branched polyamine of the therapeutic hydrogels of any of the preceding embodiments may be selected from trilysine (mol. wt. 402.5 g/mol), tetralysine (mol. wt. 530.7 g/mol), pentalysine (mol. wt. 658.9 g/mol), tris(aminoalkyl)amines (e.g., tris(2-aminoethyl)amine (mol. wt. 146.2 g/mol)), or tris(aminoalkyl)alkanes (e.g., 1,1,1-tris(aminomethyl)ethane (mol. wt. 117.2 g/mol)), among other possibilities.

In some embodiments, the branched polyamine of the therapeutic hydrogels of any of the preceding embodiments may be in the form of an organic acid salt. For example, the organic acid salt may be selected from formate, acetate, propionate, butyrate, oxalate, malonate, succinate, maleate, glutarate, glycolate, lactate, malate, citrate, or gluconate salts, among others.

In some embodiments, the branched polyamine of the therapeutic hydrogels of any of the preceding embodiments may be in the form of an inorganic salt. For example, the inorganic salt may be selected from halide salts, nitrate salts, phosphate salts, sulphate salts, or sulfonate salts, among others.

In some embodiments, the therapeutic hydrogels of any of the preceding embodiments may contain from 0.1 w/w % or less to 10 w/w % or more anionic polysaccharide, for example, ranging from 0.10 w/w % to 0.25 w/w % to 0.5 w/w % to 1.0 w/w % to 2.5 w/w % to 5 w/w % to 10 w/w % anionic polysaccharide.

In some embodiments, the anionic polysaccharide of the therapeutic hydrogels of any of the preceding embodiments may be a linear anionic polysaccharide. For example, the anionic polysaccharide may be selected from alginate, gellan gum, pectin, agaropectin, and carrageenan, among others.

In some embodiments, gellan gum is preferred. Gellan gum is a high molecular weight anionic polysaccharide gum and is generally produced by microbial fermentation. The polysaccharide is principally composed of a tetrasaccharide repeating unit of one rhamnose, one glucuronic acid, and two glucose units. Along the polysaccharide backbone are substitutions of acyl groups (glycerate and acetate) on the glucose residues. Direct recovery of the polysaccharide from the fermentation yields what is known as high acyl gellan gum. Deacylation (e.g., by alkali treatment) yields what is known as low acyl gellan gum.

In some embodiments, alginate is preferred. Alginate is a linear polysaccharide composed of mannuronate and guluronate residues. Alginate is typically produced by marine algae and some bacteria.

In some embodiments, the anionic polysaccharide of the therapeutic hydrogels of any of the preceding embodiments may be a branched anionic polysaccharide. For example, the anionic polysaccharide may be selected from guar gum, gum tragacanth, karaya gum, gum arabic, and xanthan gum, among others.

In some embodiments, the therapeutic hydrogels of any of the preceding embodiments may further contain a pH adjusting agent (i.e., a buffer). For example, the pH adjusting agent may maintain a pH of the therapeutic hydrogels between 5.5 and 7.5, among other values.

In some embodiments, the therapeutic hydrogels of any of the preceding embodiments may further contain an imaging agent. Examples of imaging agents include radiocontrast agents, fluorescent dyes, magnetic resonance imaging (MRI) contrast agents, ultrasound contrast agents and near-infrared (NIR) imaging contrast agents. Particular examples of radiocontrast agents include non-ionic radiocontrast agents, such as iohexol iodixanol, ioversol, iopamidol, ioxilan, or iopromide, among others, ionic radio contrast agents such as diatrizoate, iothalamate, metrizoate, or ioxaglate, among others, and iodinated oils, including ethiodized poppyseed oil (available as Lipiodol®). Further particular examples of imaging agents include (a) fluorescent dyes such as fluorescein, indocyanine green, or fluorescent proteins (e.g. green, blue, cyan fluorescent proteins), (b) contrast agents for use in conjunction with magnetic resonance imaging (MRI), including contrast agents that contain elements that form paramagnetic ions, such as $Gd^{(III)}$, $Mn^{(II)}$, $Fe^{(III)}$ and compounds (including chelates) containing the same, such as gadolinium ion chelated with diethylenetriaminepentaacetic acid, (c) contrast agents for use in conjunction with ultrasound imaging, including organic and inorganic echogenic particles (i.e., particles that result in an increase in the reflected ultrasonic energy) or organic and inorganic echolucent particles (i.e., particles that result in a decrease in the reflected ultrasonic energy), and (d) contrast agents for use in connection with near-infrared (NIR) imaging, which can be selected to impart near-infrared fluorescence to the hydrogels of the present disclosure, allowing for deep tissue imaging and device marking, for instance, NIR-sensitive nanoparticles such as gold nanoshells, carbon nanotubes (e.g., nanotubes derivatized with hydroxyl or carboxyl groups, for instance, partially oxidized carbon nanotubes), dye-containing nanoparticles, such as dye-doped nanofibers and dye-encapsulating nanoparticles, and semiconductor quantum dots, among others, and NIR-sensitive dyes such as cyanine dyes, squaraines, phthalocyanines, porphyrin derivatives and borondipyrromethane (BODIPY) analogs, among others.

In some embodiments, the therapeutic hydrogels of any of the preceding embodiments may further comprise a metal cation selected from Group I metal cations ($Li^+$, $Na^+$, $K^+$, $Rb^+$, $Cs^+$, $Fr^+$) and Group II metal cations ($Be^{2+}$, $Mg^{2+}$, $Ca^{2+}$, $Sr^{2+}$, $Ba^{2+}$, $Ra^{2+}$). For example, such metal cations may act as a competitor for the branched polyamine and reduce the degree of crosslinking, thereby making the therapeutic hydrogels more flowable and/or softening the therapeutic hydrogels, in some embodiments.

In some embodiments, the therapeutic hydrogels of any of the preceding embodiments may further comprise a linear polysaccharide crosslinker such as chitosan. In some embodiments such linear polysaccharide crosslinkers carry cationic charges at the pH of the gel.

In some embodiments, the therapeutic hydrogels of any of the preceding embodiments may further comprise a therapeutic agent.

In some embodiments, the therapeutic hydrogels of any of the preceding embodiments may comprise charged therapeutic agents and/or uncharged therapeutic agents. Charged therapeutic agents may be loaded into the therapeutic hydrogels by an ion exchange mechanism. Charged therapeutic agents may be electrostatically held in the therapeutic hydrogels and elute from the hydrogels in electrolytic media, such as physiological saline (0.90% w/v NaCl) or in-vivo, e.g., in the blood or tissues, to provide a sustained release of therapeutic agent over several hours, days or even weeks. Therapeutic agents without charge at physiological pH's may also be loaded into the therapeutic hydrogels. This may be particularly advantageous, for example, when rapid elution or a "burst effect" is desired, for example, for rapid therapeutic agent delivery to tissue, or when the low solubility of the therapeutic agent under physiological conditions determines the release profile rather than ionic interaction.

In some embodiments, the therapeutic hydrogels of any of the preceding embodiments may contain from 0.01 mg/ml or less to 10 mg/ml or more of one or more therapeutic agents, for example ranging from 0.01 mg/ml to 0.025 mg/ml to 0.05 mg/ml to 0.10 mg/ml to 0.25 mg/ml to 0.5 mg/ml to 1 mg/ml to 2.5 mg/ml to 5 mg/ml to 10 mg/ml.

Examples of therapeutic agents (which may also be referred to herein as pharmaceutically active ingredients) that can be incorporated into the therapeutic hydrogels of any of the preceding embodiments include small molecule therapeutic agents (defined herein as therapeutic agents having a molecular weight less than 2000 g/mol, typically less than 1500 g/mol, more typically less than 1000 g/mol) and biomolecules (e.g., polypeptides including proteins and protein fragments, such as antibodies and antibody fragments and oligopeptides, as well as polynucleotides and oligonucleotides, including nucleic acids and nucleic acid analogs such as deoxyribonucleic acids, ribonucleic acids, peptide nucleic acids, and fragments thereof).

Examples of therapeutic agents include anti-angiogenic agents, cytotoxic agents, chemotherapeutic agents, checkpoint inhibitors, immune modulatory cytokines, T-cell agonists, and STING (stimulator of interferon genes) agonists, among others.

Examples of therapeutic agents include: checkpoint inhibitors including inhibitors of the binding of PD-1 to PD-L1, inhibitors of the binding of CTLA-4 to CD80 and/or CD86, inhibitors of the binding of TIGIT to CD-112, and inhibitors of the binding of LAG-3 to MHC class II molecules; antibodies or antigen binding fragments thereof that bind to PD-1 (e.g., pembrolizumab, nivolumab domvanalimab, etc.), PD-L1 (e.g., atezolizumab, avelumab, durvalumab, etc.), LAG-3 (e.g., relatlimab, etc.), TIM-3 (e.g., LY3321367, MBG453, TSR-022, etc.), TIGIT (e.g., etigilimab, tiragolumab, vibostolimab, etc.), or CTLA-4 (e.g., ipilimumab tremelimumab, etc.); antibodies or antigen binding fragments thereof that bind to CD3, CD19, CD20, CD22, CD52, CD79B, CD30, CD33, CD38, CD52, CD79B, HER2, EGFR, VEGF, VEGFR2, EPCAM/CD3, GD2, IL-6, RANKL, SLAMF7, CCR4, PDGFRα, Nectin-4 or TROP2; immune modulatory cytokines such as IL-2, IL-12, IL-15, IL-23, interferon gamma (IFN-γ) and gm-CSF (granulocyte macrophage colony stimulating factor); T-cell agonists such as TLR3 agonists (e.g., polyinosinic:polycytidylic acid, double stranded RNAs, etc.), TLR7 agonists (e.g., TMX-202, gardiquimod, imiquimod, etc.), TLR8 agonists (e.g., VTX-2337, etc.), TLR7/8 agonists (e.g., MEDI9197, R848, resiquimod, etc.), TLR9 agonists (e.g., lefitolimod (MGN1703), tilsotolimod, CpG oligodeoxynucleotides (e.g., agatolimod), etc.); and STING agonists such as GSK 532, cyclic dinucleotides (e.g., cyclic guanosine monophosphate-adenosine monophosphate), CRD5500 (LB-061), E7766, ADU-S100, SB11285 MSA2, MK1454, TTI-10001, etc.), among others.

Examples of therapeutic agents further include: camptothecins (such as irinotecan and topotecan) and anthracyclines (such as doxorubicin, daunorubicin, idarubicin and epirubicin), antiangiogenic agents (such as vascular endothelial growth factor receptor (VEGFR) inhibitors, such as axitinib, bortezomib, bosutinib canertinib, dovitinib, dasatinib, erlotinib gefitinib, imatinib, lapatinib, lestaurtinib, masitinib, mubritinib, pazopanib, pazopanib semaxanib, sorafenib, sunitinib, tandutinib, vandetanib, vatalanib and vismodegib), microtubule assembly inhibitors (such as vinblastine, vinorelbine and vincristine), Aromatase inhibitors (such as anastrozole), platinum drugs (such as cisplatin, oxaliplatin, carboplatin and miriplatin), nucleoside analogues (such as 5-FU, cytarabine, fludarabine and gemcitabine), paclitaxel, docetaxel, mitomycin, mitoxantrone, bleomycin, pingyangmycin, abiraterone, amifostine, buserelin, degarelix, folinic acid, goserelin, lanreotide, lenalidomide, letrozole, leuprorelin, octreotide, tamoxifen, triptorelin, bendamustine, chlorambucil, dacarbazine, melphalan, procarbazine, temozolomide, rapamycin (and analogues, such as zotarolimus, everolimus, umirolimus and sirolimus), methotrexate, pemetrexed, or raltitrexed.

In some embodiments, therapeutic hydrogels of any of the preceding embodiments may additionally comprise a therapeutic and/or an imageable radioisotope. Therapeutic hydrogels comprising therapeutic radioisotopes, can be used for example in selective internal radiation therapy (SIRT) or brachytherapy such as in cancer treatment, and may be delivered in any of the manners described elsewhere herein in relation to other embodiments of the therapeutic hydrogel. In one approach, the radioisotope may be bound to the gel by ionic interaction or may be covalently attached, such as through a carrier, for example a chelating agent. In some embodiments the radioisotope may be incorporated into the gel in a particle, wherein the particle comprises the radio isotope. Such particles may be in the form of microspheres, typically having a largest diameter in the range 5 um to 500 um, particularly less than 100 um. The particles may be, for example, polymeric or maybe ceramic. One such ceramic is yttrium aluminosilicate ceramic (see for example U.S. Pat. No. 4,789,501). Further examples of ceramic microspheres are described in WO16082045 and WO05087274). Therapeutic radioisotopes include, but are not limited to, $^{177}$Lu, $^{90}$Y, $^{131}$I, $^{89}$Sr, $^{153}$Sm, $^{223}$Ra, $^{224}$Ra, $^{211}$At, $^{225}$Ac, $^{227}$Th, $^{212}$Bi, $^{213}$Bi, and/or $^{212}$Pb. In some embodiments, the therapeutic radioisotope is one or more of $^{177}$Lu, $^{90}$Y, $^{131}$I, $^{89}$Sr, $^{153}$Sm and/or $^{223}$Ra. In some embodiments, the therapeutic radioisotope is $^{90}$Y. Imageable radioisotopes include, but are not limited to $^{99m}$Tc, $^{201}$Th, $^{51}$Cr, $^{67}$Ga, $^{68}$Ga, $^{111}$In, $^{64}$Cu, $^{89}$Zr, $^{59}$Fe, $^{42}$K, $^{82}$Rb, $^{24}$Na, $^{54}$Ti, $^{44}$Sc, $^{51}$Cr and $^{177}$Lu. In some embodiments the imageable isotope is $^{99m}$Tc, $^{67}$Ga, $^{68}$Ga, $^{64}$Cu or 89Zr. In some embodiments the imageable isotope is $^{99m}$Tc. In some embodiments the imageable isotope is $^{89}$Zr.

One particular example of a ceramic particle is described in U.S. Pat. No. 4,789,501 and sold commercially as TheraSphere® (Biocompatibles UK Ltd)

The therapeutic hydrogels of any of the preceding embodiments may be provided in sterile form.

The therapeutic hydrogels of any of the preceding embodiments may be provided in several different forms. In some instances, the therapeutic hydrogels may be in the form of flowable therapeutic hydrogels, which may be injectable, for instance, from a container (e.g., a syringe barrel, vial, ampoule etc.) and through a needle or a catheter tube. In some instances, the therapeutic hydrogels may be in the form of a free-standing three-dimensional shape. For example, the therapeutic hydrogels may be in the form of microparticles or microspheres or may be in the form of larger implantable dosage forms such as beads, pellets, plugs, discs, and so forth.

Other embodiments of the present disclosure relate to medical compositions comprising the therapeutic hydrogels of any of the preceding embodiments.

For example, in some embodiments, the medical compositions are therapeutic agent delivery depots that comprise the therapeutic hydrogels of any of the preceding embodiments. Such therapeutic agent delivery depots may release therapeutic agents in a controlled manner for local, systemic, or targeted therapeutic agent delivery.

In some embodiments, the medical compositions are embolic agents that comprise the therapeutic hydrogels of any of the preceding embodiments.

In some embodiments, the medical compositions are tissue sealants that comprise the therapeutic hydrogels of any of the preceding embodiments.

In some embodiments, the medical compositions are tissue spacers that comprise the therapeutic hydrogels of any of the preceding embodiments.

In some embodiments, the medical compositions are tissue augmentation compositions (including dermal fillers) that comprise the therapeutic hydrogels of any of the preceding embodiments.

In some embodiments, the medical compositions are scaffolds for tissue regeneration and/or cellular growth that comprise the therapeutic hydrogels of any of the preceding embodiments.

In some embodiments, the medical compositions are surgical adhesion prevention barriers that comprise the therapeutic hydrogels of any of the preceding embodiments.

In some embodiments, the medical compositions are implantable wound dressings that comprise the therapeutic hydrogels of any of the preceding embodiments.

Still other embodiments of the present disclosure relate to medical procedures that employ the therapeutic hydrogels or the medical compositions of any of the preceding embodiments.

For example, in some embodiments, the medical procedures are methods of local or systemic therapeutic agent release that comprise delivering (e.g., by injecting, implanting, spraying, etc.) the therapeutic hydrogels or the medical compositions of any of the preceding embodiments to a patient (e.g., onto tissue of the patient, into tissue of the patient, between tissues of the patient, etc.).

In some embodiments, the medical procedures are methods of treatment that comprise delivering (e.g., by injecting, implanting, spraying, etc.) the therapeutic hydrogels or the medical compositions of any of the preceding embodiments into or onto a tumor of a patient, wherein the therapeutic agent is released into the tumor.

In some embodiments, the medical procedures are methods of tissue embolization that comprise delivering the therapeutic hydrogels or the medical compositions of any of the preceding embodiments into one or more blood vessels (e.g. a feeder artery) feeding the tissue.

In some embodiments, the medical procedures are methods of spacing a first tissue from a second tissue that comprise delivering (e.g., injecting, implanting, etc.) the therapeutic hydrogels or the medical compositions of any of the preceding embodiments between the first tissue and the second tissue (e.g., between prostate tissue and rectal tissue).

In some embodiments, the medical procedures are methods of sealing tissue that comprise applying the therapeutic hydrogels or the medical compositions of any of the preceding embodiments onto the tissue. The methods include topically applying the therapeutic hydrogels or medical compositions to tissue at the surgical site in an amount effective to seal the tissue.

In some embodiments, the medical procedures are methods of preventing surgical adhesions that comprise applying the therapeutic hydrogels or the medical compositions of any of the preceding embodiments onto tissue at a surgical site, whereby post-surgical adhesions at the surgical site in a patient are inhibited. The methods include topically applying the therapeutic hydrogels to tissue at the surgical site in an amount effective to inhibit the formation of adhesions during healing.

In some embodiments, the medical procedures are methods of tissue augmentation that comprise delivering (e.g., by injecting, implanting, etc.) the therapeutic hydrogels or the medical compositions of any of the preceding embodiments into tissue of a patient or between tissues of a patient (e.g., to alter the contour of tissue, to increase the volume of the tissue, etc.).

In some embodiments, the medical procedures are methods of regenerating tissue of a patient that comprise delivering (e.g., by injecting, implanting, spraying, etc.) a tissue scaffold that comprises the therapeutic hydrogels or the medical compositions of any of the preceding embodiments to a patient (e.g., into tissue of the patient, onto tissue of the patient, or between tissues of the patient, etc.).

In some embodiments, the medical procedures are methods of haemostasis in a patient that comprise delivering (e.g., by injecting, implanting, spraying, etc.) the therapeutic hydrogels or the medical compositions of any of the preceding embodiments to a patient (onto tissue of a patient, into tissue of a patient, including into blood vessels of the patient).

In yet further embodiments, the present disclosure relates to the use of the therapeutic hydrogels or the medical compositions of any of the preceding embodiments, in the manufacture of a medicament for the treatment of diseases, such as cancer, particularly solid tumors. Such cancers include, but are not limited to, cancers of the liver (such as hepatocellular carcinoma and metastases of remote tumors to the liver such as metastatic colorectal cancer, neuroendocrine tumors, metastatic Barrett's esophagus etc.), cancers of the Lungs, breast, kidney, head and neck, esophagus, skin, pancreas, adrenal glands, brain, stomach and gut.

The present disclosure also relates to the use of any of the pharmaceutically active ingredients herein in the in the manufacture of a medicament for the treatment of such diseases wherein the active ingredient is incorporated into a hydrogel of any of the above embodiments. The present disclosure also relates to the use of any of the active ingredients herein in the treatment of such diseases wherein the active ingredient is incorporated into a hydrogel of any of the above embodiments. The therapeutic hydrogels and compositions may be particularly used where the hydrogel is delivered by injecting, implanting, spraying, etc.

In embodiments, a therapeutic hydrogel for the local delivery of treatment agents is formed. The therapeutic hydrogel includes the following: (a) 0.5-2.5 w/w % anionic polysaccharide (e.g., gellan gum (low or high acyl, depending on the degree of acyl substitution) or alginate), (b) 0.01-3.0 w/w % branched polyamine (e.g., acetate forms of polylysines including trilysine acetate, tetralysine acetate, pentalysine acetate, etc.), (c) a therapeutic agent, and (d) optionally, other agents such as pH adjusting agents, preservatives, and/or contrast agents, among others.

In one specific approach to the embodiments described herein, the therapeutic hydrogel is a gellan gum, cross linked with trilysine, which may be prepared as described above.

The hydrogel is typically formed by heating a solution of the anionic polysaccharide to a temperature suitable for allowing the polysaccharide to hydrate. This typically ranges from 62 Celsius to 90 Celsius. The polysaccharide may be allowed to hydrate, typically for a period ranging from 30 minutes to 3 hours. If desired, the solution may be agitated, for example by impellers suitable for blending high viscosity materials (otherwise phase separation may occur).

After hydration of the anionic polysaccharide, the gel may be cooled to a temperature that prevents possible damage to any active ingredient that may be incorporated. Temperatures below 40 Celsius are generally suitable. At this point the therapeutic agent may be added, if used, followed by addition of the crosslinker. The therapeutic agent and the crosslinker may be added with continuous stirring at controlled temperatures (e.g., in a jacketed, temperature-controlled mixing vessel).

Ingredients may be sterilized prior to formulation. Ingredients can be loaded in an aseptic manner, or ingredients can be sterilized after filling the composition into syringes or other containers (e.g., while warm).

Example

A therapeutic hydrogel is formed from the following: 1.5 w/w % low acyl gellan gum, water for injection (WFI) as solvent, 0.03 w/w % trilysine-acetate (TLA) as crosslinker. Gellan gum was added to WFI at a temperature above 80 Celsius. Continuous stirring with impeller was employed for high viscosity materials. After 2 hours hydration time, the mixtures was cooled. IgG was added at a temperature of 38 Celsius. At this stage a lower volume of the gel was transferred to a beaker with a magnetic stirring bar. IgG was then added, followed by TLA after 1 minute mixing. The loaded, crosslinked mixture was stirred for a further 3 minutes, then filled into syringes. Syringes were refrigerated below 5 Celsius overnight then the samples were tested for drug release characteristics.

IgG was loaded into the therapeutic hydrogel as an active ingredient surrogate for an anti-PD1 loaded gel. Release profiles are measured by injecting 1 g hydrogel samples into well plates. 6 ml calcium-free Dulbecco PBS solution was used as a collection medium. 100 ul samples were drawn from the PBS at designate timepoints and the samples were transferred into 96 well plates. Release profile was measured by using a BioTek Microplate Reader (BioTek Instruments, Inc., Winooski, VT, USA) using absorbance measurement at 280 nm wavelength. Results are shown in the FIGURE, which illustrates cumulative release % as a function of time for the IgG. Release is thought to be primarily controlled by diffusion.

The therapeutic hydrogel loaded with the therapeutic agent can be injected submucosally or can be used for local treatments (e.g. intratumorally for the local delivery and sustained release of anti-cancer agents).

The invention claimed is:

1. A therapeutic hydrogel comprising: (a) an anionic polysaccharide, and (b) a branched polyamine, wherein the anionic polysaccharide is negatively charged at a pH of the therapeutic hydrogel, wherein the branched polyamine has a molecular weight that is less than 2000 g/mol, is positively charged and comprises two or more positively charged, primary amine groups at the pH of the therapeutic hydrogel, and wherein the branched polyamine ionically crosslinks the anionic polysaccharide.

2. The therapeutic hydrogel of claim 1, wherein the branched polyamine comprises three or more positively charged, primary amine groups at the pH of the therapeutic hydrogel.

3. The therapeutic hydrogel of claim 1, wherein the branched polyamine comprises between three and ten positively charged, primary amine groups at the pH of the therapeutic hydrogel.

4. The therapeutic hydrogel of claim 1, wherein the therapeutic hydrogel has a pH that ranges from 5.5 to 7.5.

5. The therapeutic hydrogel of claim 1, wherein the branched polyamine is in the form of an organic acid salt.

6. The therapeutic hydrogel of claim 1, wherein the anionic polysaccharide is gellan gum and wherein the branched polyamine is trilysine acetate.

7. The therapeutic hydrogel of claim 1, wherein the branched polyamine is an oligomeric branched polyamine having from 2 to 10 monomer residues.

8. The therapeutic hydrogel of claim 7, wherein the oligomeric branched polyamine is a branched peptide oligomer that comprises a plurality of lysine residues.

9. The therapeutic hydrogel of claim 1, where the anionic polysaccharide is a linear anionic polysaccharide or a branched anionic polysaccharide.

10. The therapeutic hydrogel of claim 1, wherein the therapeutic hydrogel is a flowable therapeutic hydrogel.

11. The therapeutic hydrogel of claim 1, further comprising an imaging agent selected from fluorescent dyes, magnetic resonance imaging (MRI) contrast agents, ultrasound contrast agents, radiocontrast agents, and near-infrared (NIR) contrast agents.

12. The therapeutic hydrogel of claim 1, wherein the therapeutic hydrogel further comprises a cation selected from Group I metal cations and Group II metal cations.

13. The therapeutic hydrogel of claim 1, further comprising chitosan.

14. The therapeutic hydrogel of claim 1, wherein the therapeutic hydrogel further comprises a therapeutic agent selected from anti-angiogenic agents, cytotoxic agents, chemotherapeutic agents, checkpoint inhibitors, immune modulatory cytokines, T-cell agonists, and STING (stimulator of interferon genes) agonists.

15. A therapeutic hydrogel comprising an anionic polysaccharide crosslinked by a branched polyamine, wherein the branched polyamine comprises at least three primary amine groups and has a molecular weight that is less than 2000 g/mol.

16. The therapeutic hydrogel of claim 15, wherein the branched polyamine comprises between three and ten primary amine groups.

17. A therapeutic hydrogel comprising: (a) an anionic polysaccharide, and (b) a branched polyamine, wherein the anionic polysaccharide is negatively charged at a pH of the therapeutic hydrogel, wherein the branched polyamine has a molecular weight that is less than 2000 g/mol, is positively charged, and comprises three or more positively charged, primary amine groups at the pH of the therapeutic hydrogel, wherein the anionic polysaccharide is a linear anionic polysaccharide, wherein the branched polyamine is a peptide oligomer and is in the form of an organic acid salt, and wherein the branched polyamine is ionically crosslinked by the anionic polysaccharide.

18. The therapeutic hydrogel of claim 17, wherein the linear anionic polysaccharide is gellan gum.

19. The therapeutic hydrogel of claim 18, wherein the branched polyamine is a polylysine acetate.

20. The therapeutic hydrogel of claim 18, wherein the branched polyamine is trilysine acetate.

* * * * *